United States Patent [19]

Pelletier et al.

[11] Patent Number: 4,920,219

[45] Date of Patent: Apr. 24, 1990

[54] SUBSTITUTED SATURATED AND UNSATURATED INDOLE QUINOLINE AND BENZAZEPINE CARBOXAMIDES AND THEIR USE AS PHARMACOLOGICAL AGENTS

[75] Inventors: Jeffrey C. Pelletier, Lansdale, Pa.; Raymond D. Youssefyeh, Princeton Junction, N.J.; Henry F. Campbell, North Wales, Pa.

[73] Assignee: Rorer Pharmaceutical Corp., Ft. Washington, Pa.

[21] Appl. No.: 277,582

[22] Filed: Nov. 29, 1988

[51] Int. Cl.$^5$ .................. C07D 453/02; C07D 215/00; C07D 209/34

[52] U.S. Cl. .................................... 540/523; 546/133; 546/165; 548/486

[58] Field of Search ................ 540/523; 546/133, 165; 548/486

[56] References Cited

U.S. PATENT DOCUMENTS 4,599,420 7/1986 Hadley et al. ...................... 546/133

Primary Examiner—Mukund J. Shah
Assistant Examiner—E. C. Ward
Attorney, Agent, or Firm—James A. Nicholson; Martin Savitzky; Imre Jim Balogh

[57] ABSTRACT

Certain specific substituted azabicyclic carboxiamides and their valuable use as 5-HT3 antagonists having CNS and gastric prokenetic activity void of any $D_2$ receptor binding properties are disclosed.

7 Claims, No Drawings

SUBSTITUTED SATURATED AND UNSATURATED INDOLE QUINOLINE AND BENZAZEPINE CARBOXAMIDES AND THEIR USE AS PHARMACOLOGICAL AGENTS

FIELD OF THE INVENTION

This invention relates to azabicyclic substituted carboxamide compounds which exhibits 5-HT$_3$ antagonist properties including CNS, anti-emetic and gastric prokinetic activity which are void of any significant D$_2$ receptor binding affinity. This invention also relates to pharmaceutical compositions and methods for the treatment of gastrointestinal and mental disorders using said compounds. This invention describes also novel processes for their preparation.

5-Hydroxytryptamine, abbreviated "5HT", is commonly known as serotonin. Serotonin is found throughout the body including the gastrointestinal tract, platelets, spleen and brain, and appears to be involved in a great number of physiological processes such as a neurotransmitter at certain neurones in the brain, and is implicated in a number of central nervous system (CNS) disorders. Additionally, serotonin appears to act as a local hormone in the periphery: it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors have been identified and the following assignment of receptors has been proposed: D-receptors are 5HT$_2$-receptors; M-receptors are termed 5HT$_3$-receptors; and all other receptors, which are clearly not 5HT$_2$ or 5HT$_3$, should be referred to as 5HT$_1$-like.

5HT$_3$-receptors have been located in non-neurological tissue, brain tissue, and a number of peripheral tissues related to different responses. It has been reported that 5HT$_3$-receptors are located on peripheral neurones where they are related to serotonin's (excitatory) depolarizing action. The following subtypes of 5HT$_3$ receptor activity have been reported: 5HT$_{3B}$ subtype involving postganglionic sympathetic and parasympathetic neurones, leading to depolarization and release of noradrenaline and acetylcholine, respectively; 5HT$_{3C}$ subtype involving on enteric neurones, where serotonin may modulate the level of acetylcholine; and 5HT$_{3A}$ subtype involving on sensory nerves such as those involved in the stimulation of heart nerve endings to produce a reflex bradycardia, and also in the perception of pain.

Highly selective 5HT$_3$-antagonists have been shown to be very effective at controlling and preventing emesis (vomiting) induced by chemotherapy and radiotherapy in cancer patients. The anti-emetic effects of 5HT$_3$-antagonists in animals exposed to cancer chemotherapy or radiation are similar to those seen following abdominal vagotomy. The antagonist compounds are believed to act by blocking 5HT$_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an axon reflex mechanism, than providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific 5HT$_3$ receptors on the primary afferent neurones.

5HT$_3$-antagonists are also reported to exert potential antipsychotic effects, and are believed to be involved in anxiety. Although not understood well, the effect is believed to be related to the indirect blocking of serotonin 5HT$_3$-mediated modulation of dopamine activity.

Many workers are investigating various compounds having 5HT$_3$-antagonist activity.

Reported Developments

The development of 5-HT$_3$ agents originated from work carried out with metoclopramide (Beecham's Maxolon, A. H. Robins' Reglan), which is marketed for use in the treatment of nausea and vomiting at high doses. Metoclopramide is a dopamine antagonist with weak 5HT$_3$-antagonist activity, which becomes more prominent at higher doses. It is reported that the 5HT$_3$ activity and not the dopamine antagonism is primarily responsible for its anti-emetic properties. Other workers are investigating this compound in connection with the pain and vomiting accompanying migraine.

Merrel Dow's compound MDL-72222 is reported to be effective as an acute therapy for migraine, but toxicity problems have reportedly ended work on this compound. Currently four compounds A. H. Robins' Zacopride, Beecham's BRL-43694, Glaxo's GR-38032F and Sandoz' ICS-205–930 are in clinical trials for use in chemotherapy-induced nausea and vomiting. GR-38032F is also in clinical trials for the treatment of anxiety and schizophrenia. Zacopride is reported to be in clinical trials for anxiety, while ICS-205–930 is reported useful in the treatment of carcinoid syndrome.

Compounds reported as gastroprokinetic agents include Beecham's BRL-24924, which is a serotonin-active agent for use in gut motility disorders such as gastric paresis, reflux esophagitis, and is know to have also 5HT$_3$-antagonist activity.

Metoclopramide, Zacopride, Cisapride and BRL-24924 are characterized by a carboxamide moiety situated para to the amino group of 2-chloro-4-methoxy aniline. BRL-43694, ICS-205930, GR-38032F and GR-65630 are characterized by a carbonyl group in either the 3-position of indole or N-benzoate, while Zacopride, BRL-24924, BRL-43694, ICS-205930 have also bridged azabicyclic groups in the form of a carboxamide or carboxylic ester.

Dibenzofurancarboxamides and 2-carboxamide-substituted benzoxepines are reported to have 5HT$_3$-antagonist and gastroprokinetic activity in copending application serial nos. 152,112, 152,192, and 168,824, all of which are assigned to the same assignee as the present application.

Summary of the Invention

This invention relates to bicyclic benzomonoazacyclic carboxamide compounds having 5-HT3 antagonist activity gastric prokinetic, anti-emetic activity and lack D$_2$ receptor binding activity, and to therapuetic compositions comprising said compounds. Preferred compounds of this invention are described by general Formula I:

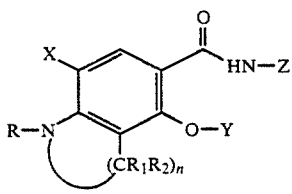

wherein:

X is hydrogen, alkyl, alkoxy, hydroxy, amino, mono- and di-alkylamino, halo, trifluoromethyl, nitro, sulfamyl, mono- and di-alkylsulfamyl, alkylsulfonyl, carboxy, carbalkoxy, carbamyl or mono- and di-alkylcarbamyl;

R is hydrogen, alkyl, formyl or acyl;

R$_1$ and R$_2$ are independently hydrogen or alkyl;

vicinal R$_2$ groups may together may be —(CH$_2$)$_a$— where a is 1 to 4, thus forming a 3 to 6 membered ring;

vicinal R$_1$ groups together may form a double bond;

when n is 3 then vicinal R and R$_1$ groups together may form a double bond;

n is 2 to 4;

Y is hydrogen, alkyl, alkenyl, aralkyl,

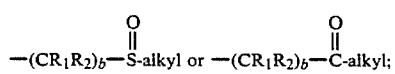

b and d are 1 to 4;

Z is —(CR$_1$R$_2$)$_d$—NR$_1$R$_2$,

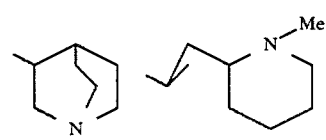

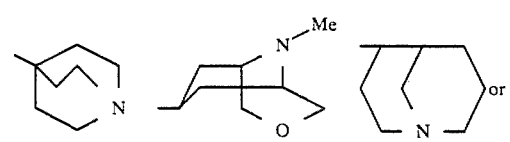

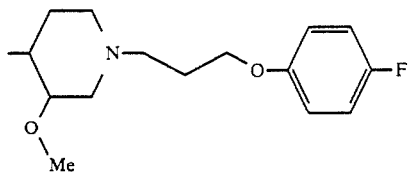

and pharmaceutically acceptable salts thereof.

This invention relates also to pharmaceutical compositions including an effective therapeutic amount of the aforementioned bicyclic benzomonoazacyclic carboxamide compounds of Formula I and therapeutic methods for the treatment of a patient suffering from gastrointestinal disorders and/or psychochemical imbalances in the brain by administering said pharmaceutical composition.

Detailed Description

As employed above and throughout the disclosure, the following, unless otherwise indicated, shall be understood:

The choice of a R$_1$ or R$_2$ substituent group for a particular position in the compound of Formula I does not limited other R$_1$ or R$_2$ groups to the same substituent. ¢Alkyl" means a saturated aliphatic hydrocarbon which may be either straight or branched-chained containing from about 1 to about 6 carbon atoms. "Lower alkyl" means an alkyl group as above, having 1 to about 4 carbon atoms. "Aralkyl" means an alkyl group substituted by an aryl radical where aryl means a phenyl or phenyl substituted with one or more substituents which may be alkyl, alkoxy, amino, nitro, carboxy, carboalkoxy, cyano, alkyl amino, halo, hydroxy, hydroxyalkyl, mercaptyl, alkyl mercaptyl, carboalkyl or carbamoyl. The preferred aralkyl groups are benzyl or phenethyl.

"Carbamyl" means a group of the formula

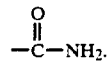

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Acyl" means an organic radical derived from an organic acid, a carboxylic acid, by the removal of its acid hydroxyl group. Preferred acyl groups are benzoyl and lower alkyl carboxylic acids groups such as acetyl and propionyl.

The chemical nomenclature for the Z groups defined above are presented below.

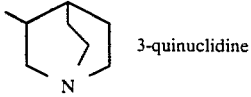 3-quinuclidine

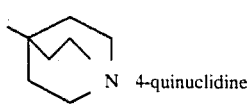 4-quinuclidine

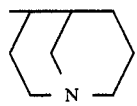
4-(1-azabicyclo[3.3.1]nonane)

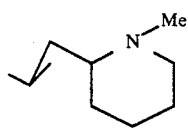
3-(9-methylazabicyclo[3.3.1]-nonane)

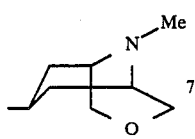
7-(3-oxo-9-methylazabicyclo[3.3.1]nonane)

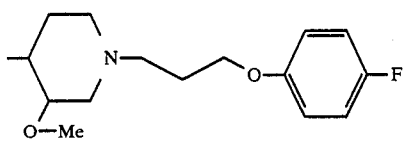
4-[3-methoxy-1-(3-[4-fluorophenoxy]propyl)piperidine]

Certain of the compounds of the present invention may exist in enolic or tautomeric forms, and all of these forms are considered to be included within the scope of this invention.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, maleic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

A preferred class of compounds is described by Formula I where:

X is hydrogen, hydroxy, amino, mono- and di-loweralkylamino, halo, trifluoromethyl, sulfamyl, mono- and di-loweralkylsulfamyl or loweralkylsulfonyl;

R is hydrogen or loweralkyl;

$R_1$ and $R_2$ are independently hydrogen or loweralkyl;

vicinal $R_2$ groups together may be, —$(CH_2)_a$— where a is 1 to 4, thus forming a 3 to 6 member ring;

n is 2 to 4;

Y is loweralkyl, —$(CR_1R_2)_b$-SO-loweralkyl or —$(CR_1R_2)_b$-CO-loweralkyl;

b and d are 1 to 3; and

Z is —$(CR_1R_2)_d$—$NR_1R_2$,

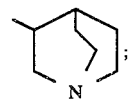

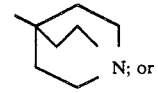

and pharmaceutically acceptable salts thereof.

The more preferred compounds are those of Formulae II, III and IV:

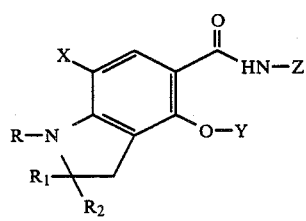

II

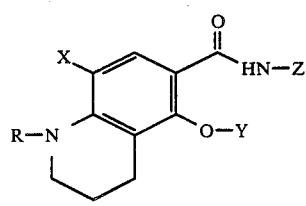

III

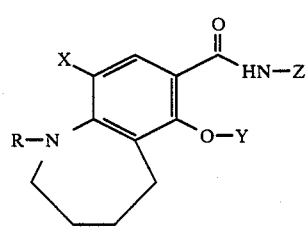

IV where

X is hydrogen or halo;

R is hydrogen, methyl or ethyl;
$R_1$ and $R_2$ are independently hydrogen, methyl or ethyl;
Y is methyl, ethyl, propyl, i-propyl, butyl, i-butyl, sec-butyl, t-butyl, pentyl, —$(CR_1R_2)_b$—SO-loweralkyl of 1-3 carbon atoms, —$(CR_1R_2)_b$—CO-loweralkyl of 1-3 carbon atoms;
b is 1 to 3; and
Z is

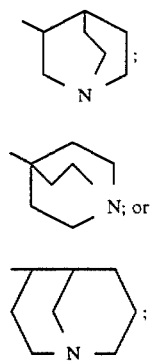

and pharmaceutically acceptable salts thereof.

The most preferred compounds are those of Formulae II, III and IV where:
X is chloro or bromo;
R is hydrogen or methyl;
$R_1$ and $R_2$ are independently hydrogen, methyl or ethyl;
Y is methyl; and
Z is

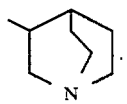

The compounds of this invention may be prepared by the following general procedure:

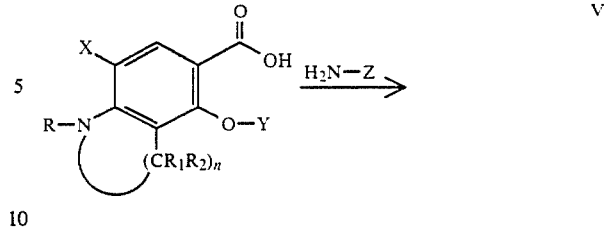

Condensation of the carboxylic acid of a substituted (1H)indole, quinoline, (1H)-1-benzazepine or the dihydro or tetrahydro forms thereof of Formula V or their acid halides or esters with an amine of the formula $H_2N$-Z results in the corresponding carboxamide.

In general this reaction may be carried out at decreased temperatures, such as 0° C. by adding ethyl chloroformate to a reaction mixture of the acid in chloroform in the presence of triethylamine. This is then reacted with the amine of the formula $H_2N$-Z to obtain the desired product. Condensation may also be carried out in the presence of a dehydrating catalyst such as a carbodiimide in a solvent at normal temperatures.

The starting materials of Formula V, that is the carboxylic acids of the substituted saturated and unsaturated indoles, quinolines and benzazepines and more specifically (1H) indole, (1H)-2,3-dihydroindole, quinoline, 1,2,3,4-tetrahydroquinoline, (3H)-4,5-dihydro-1-benzazepine, (1H)-1-benzazepine and (1H)-2,3,4,5-tetrohydro-1-benzazepine are also novel. They may be prepared by the reaction Schemes I, II and III below. The preparation of the [5,6] bicyclic ring compounds is shown in Reaction Scheme I, the preparation of the [6,6] bicyclic ring compounds is shown in Reaction Scheme II, and the preparation of the [6,7] bicyclic ring systems is shown in Reaction Scheme III.

Scheme I

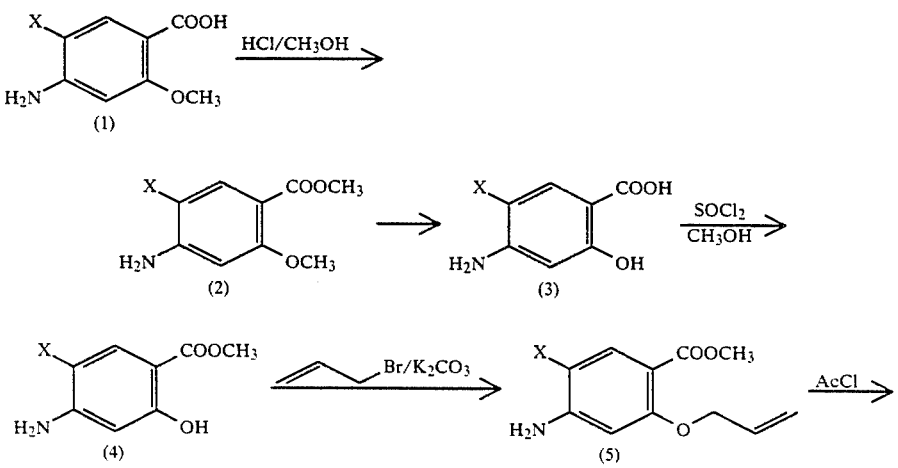

Scheme I

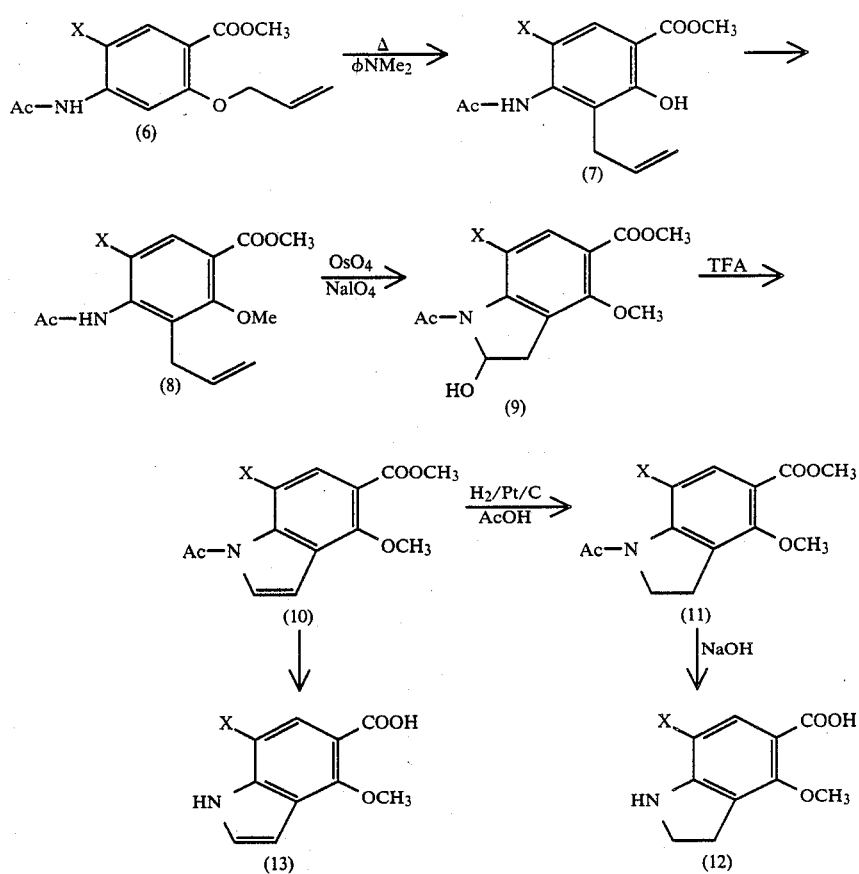

Esterification of a substituted 2-methoxy-4-aminobenzoic acid (1) followed by demethylation of the alcohol and ester using boron tribromide in a nonpolar solvent results in the 4-aminosalicylic acid (3). Esterification to the salicylate (4) followed by treatment with allylbromide under basic conditions gives the allylalcohol (5). The amine may then be protected by acetylation of this group in the usual manner in a pyridine medium (6). Claisen rearrangement at high temperature results in the alkyl 3-allyl-4-acetylaminosalicylate (7). The alcohol is then alkylated (8) and cyclized preferably by treatment with osmium tetroxide in a nonpolar medium in the presence of sodium periodate which results in the corresponding 2-hydroxy-(1H)-2,3-dihydroindole (9). Dehydration with triflouroacetic acid results in the formation of the 1-acetylindole compound (10). This may then be hydrogenated in the usual manner to the 1-acetyl-2,3-dihydroindole (11) which may then be treated with base to deacetylate the nitrogen and obtain the desired 4-alkoxy-5-carboxy-(1H)-2,3-dihydroindole (12). The 1-acetylindole (10) may also be deacetylated to obtain 4-alkoxy-5-carboxy-(1H)indole (13).

Scheme II

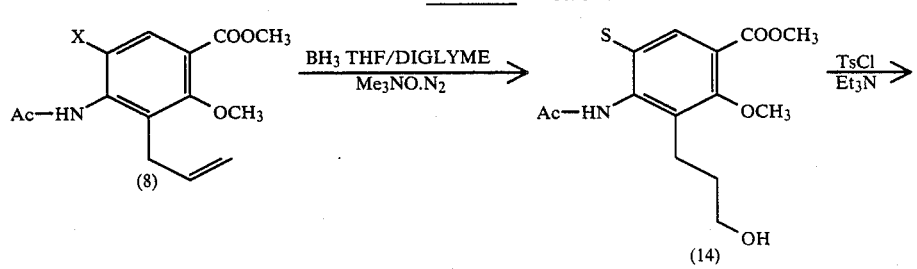

-continued
Scheme II

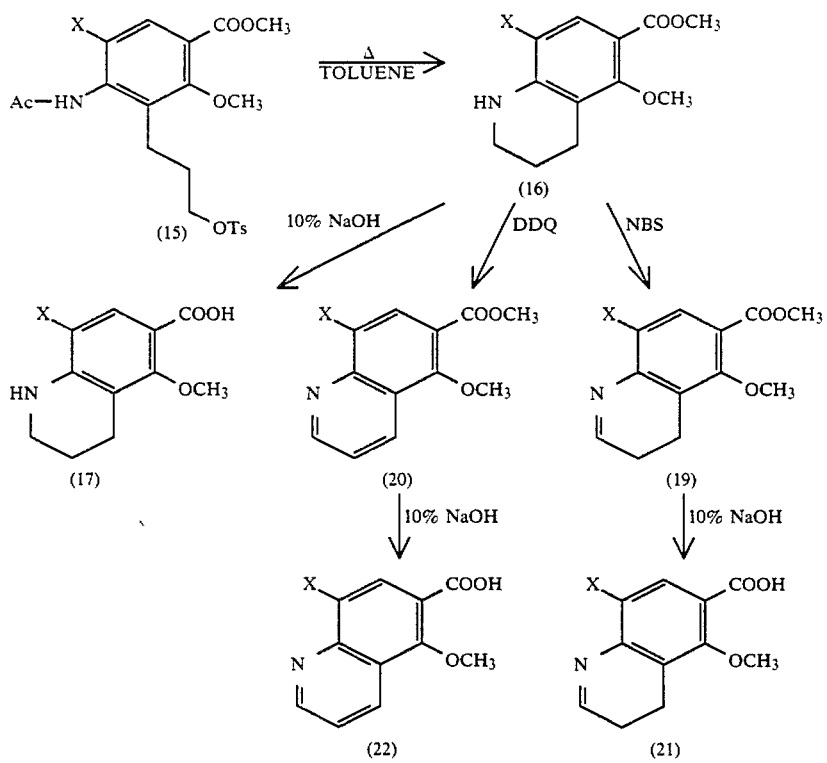

When the 2-alkoxy-3-allyl-4-acetylamino benzoate (8) is treated with borane-tetrahydrofuran in THF-diglyme followed by treatment with trimethylamine N-oxide dihydrate at raised temperatures the 3-(3-hydroxypropyl)benzoate (14) results. The tosylate is then made in the usual manner with tosylchloride and triethylamine and is deacetylated to form (15) which is ring closed at raised temperatures in a nonpolar medium such as toluene. The resulting 1,2,3,4-tetrahydroquinoline (16) is next treated with 10%NaOH to form the acid (17). Dehydration of the ester (16) preferably using N-bromosuccinimide gives the 3,4-dihydroquinoline product (19). Alternatively, using dichlorodicyanoquinone (DDQ) at raised temperatures results in the quinoline product (20). The acids (20) and (21) are obtained by desterification with base as above.

Scheme III

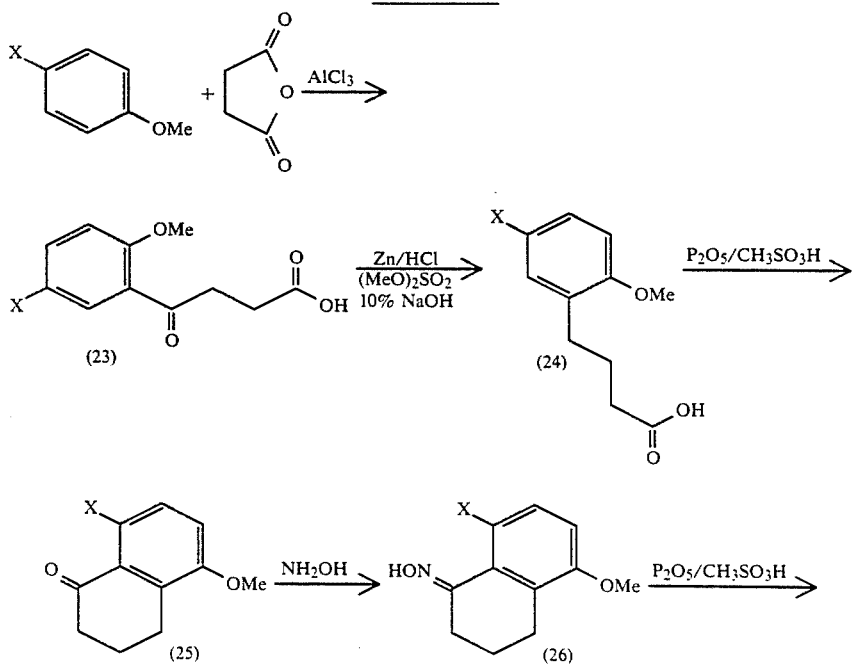

Scheme III

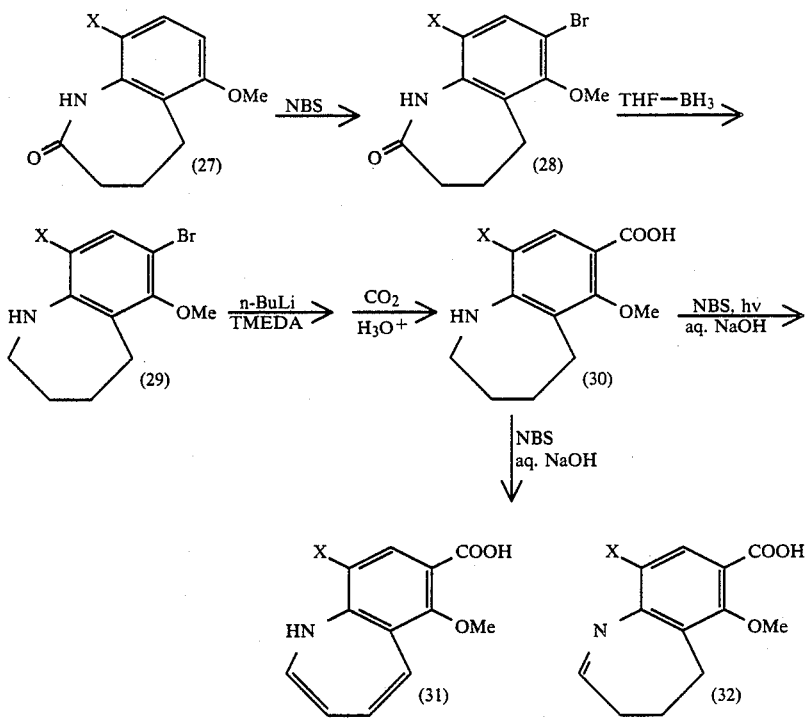

Friedel-Crafts acylation of a 4-substituted anisole with succinic anhydride results in the 2-(3-carboxypropionyl)anisole compound (23). Clemmensen reduction of the ketogroup using zinc amalgan and hydrochloric acid gives the butyric acid (24). Ring closure in the presence of phosphorous pentoxide in methane sulfonic acid results in the tetralone (25). When the latter is treated with hydroxylamine the ketooxime product results (26). Beckmann rearrangement with phosphorus pentoxide in methane sulfonic acid gives the ring enlargement to the benzazepinone (27). Bromination of the latter with NBS gives 7-bromobenzazepinone (28). Reduction of the ketofunction using borane-THF complex provides the benzazepine (29). Conversion of the bromo group to a carboxy group maybe effected by treatment with n-butyl lithium and tetramethylethylenediamine followed by reacting with carbon dioxide resulting in the 9-substituted-6-methoxy-(1H)-2,3,4,5-tetrahydro-1-benzazepine-9-carboxylic acid (30). Dehydration of the tetrahydrobenzazepine by irradiating in the presence of N-bromosuccinimide gives the (1H)-1-benzazepine product (31) while milder treatment with N-bromosuccinimide at 0° C. in basic solution gives (3H)-4,5-dihydro-1-benzazepine (32).

When it is desired that Y be other than methyl, when n is 2 or 3, the Y group other than methyl may be added to the 3-allyl-4-aminosalicylate of compound (7) when the alcohol is converted to the ether by using the corresponding sulfate in place of dimethylsulfate.

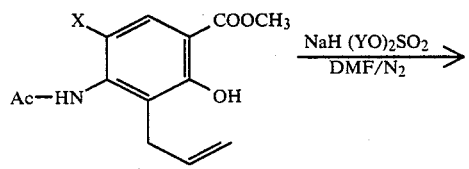

On the other hand when n is 4, thus forming the benzazepine ring system, it is preferable to start the synthesis with the desired Y group present. Thus the starting material should be of the formula

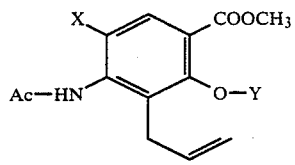

Appropriately desired end products having various X substituents can be prepared by using suitable reactions in order to convert one group to another. Thus, for example when X is chloro, bromo or iodo, this may be reacted with cuprous cyanide in quinoline at about 150° C. to produce those compounds where X is cyano. This in turn may be converted to the acids, esters or amides.

The halo group may also be reacted with triflouromethyliodide and copper powder at about 150° C. in DMF to obtain those compounds where X is CF$_3$. Halo may also be reacted with cuprous methanesulfinate in quinoline at 150° C. to obtain the methylsulfonyl substituent.

When X is nitro, selective hydrogenation results in the corresponding amine, which may be mono- or dialkylated with loweralkyl halides or sulfates. The amino group may also be diazotized to the diazonium flouride which is then thermally decomposed to the flourine derivative compound. The amine may also be diazotized and heated in an aqueous medium to form the alcohol or heated in an alcohol to form the alkoxy compound. Chlorosulfonation of the amine group may form the corresponding sulfamyl or mono- and di-alkylsulfamyl groups.

Depending on the chemistry involved in the synthesis, these reactions may be carried out at any appropriate stage of the synthesis. For example, the synthesis of X starting from $NO_2$ may be done after the ring closed molecule or even after the carboxamide is prepared.

The compounds of this invention may contain at least one asymmetric carbon atom and may have two centers when $R_1$ is not the same as $R_2$. As a result, the compounds of Formula I may be obtained either as racemic mixtures or as individual enantiomers. When two asymmetric centers are present the product may exist as a mixture of two diasteromers. The product may be synthesized as a mixture of the isomers and then desired isomer separated by conventional techniques such as chromatography or fractional crystallization from which each diasteromer may be resolved. On the other hand, synthesis may be carried out by known sterospecific processes using the desired form of the intermediate which would result in obtaining the desired specificity.

It is convenient to carry out condensation of the intermediate carboxylic acids mentioned above with the amines of the formula $H_2N$-Z using the sterospecific materials. Accordingly, the acid may be resolved into its stereoisomers prior to condensation with resolved amine.

The compounds of this invention may be prepared by the following representative examples.

EXAMPLE 1

The preparation of (N-1-Azabicyclo[2.2.2]Oct-3-yl)-7-Chloro-4-Methoxy-2,3-Dihydroindole-5-Carboxamide

Step 1. Methyl 2-methoxy-4-amino-5-chlorobenzoate

HCl gas is bubbled through a suspension of 2-methoxy-4-amino-5-chlorobenzoic acid (39 g) in methanol (600 ml) while cooled in an ice bath for 20 minutes. The mixture is evaporated affording the desired product as a solid which is used in the next step.

Step 2. 4-Amino-5-chlorosalicylic acid

A 0.1 molar solution of boron tribromide in methylene chloride (600 ml) is added to stirred suspension of methyl 2-methoxy-4-amino-5-chlorobenzoate (37 g) in methylene chloride (500 ml). After stirring for 20 hrs, the mixture is poured into ice water, and the precipitate remaining in the reaction container is washed in the ice water mixture with a solution of 5.5N NaOH (600 mls). The aqueous layer is separated and acidified to pH3. The resulting precipitate is filtered, washed with water and dried affording 4-amino-5-chlorosalicylic acid which is used directly in the next step.

Step 3. Methyl 4-amino-5-chlorosalicylate

4-Amino-5-chlorosalicylic acid (24 g) is added to a stirred solution of thionyl chloride (30 ml) in methanol (300 ml) cooled to 0° C., and the mixture is stirred under reflux for 18 hours. The reaction mixture is evaporated and the residue is recrystallized from EtOH-$H_2O$ to give methyl 4-amino-5-chlorosalicylate which is used directly in the next step.

Step 4. Methyl 2-allyloxy-4-amino-5-chlorobenzoate

A mixture of methyl 4-amino-5-chlorosalicylate (5 g), allyl bromide (12.6 g), ground K2CO3 (30 g) and acetone (120 ml) is stirred at reflux for 5 hours and cooled to 25° C. The mixture is partitioned between methylene chloride and $H_2O$, the organic layer is separated, dried (MgSO4), filtered and evaporated. The residue is recrystallized from hexanechloroform affording the desired product as a crystalline solid (M.P. 107°-109° C.).

Step 5. Methyl 2-allyloxy-4-acetylamino-5-chlorobenzoate

Acetyl chloride (6.5 g) is added dropwise to a stirring solution of the amine of step 4 above (5 g) in pyridine (80 ml) cooled in an ice bath. The reaction mixture is allowed to warm to RT with stirring for 45 minutes. Water is added, the mixture again cooled in ice, and partitioned between $H_2O$ and $CH_2Cl_2$. The organic layer is separated and washed successively with $H_2O$, 10% HCl, aqueous saturated NaHCO3, dried, filtered and evaporated affording a solid residue which is recrystallized from Hexane-Ethyl acetate, M.P. 110°-112° C. NMR (90 MHz, DMSO-$d_6$) shows the correct compound.

Step 6. Methyl 3-allyl-2-hydroxy-4-acetylamino-5-chlorobenzoate

A solution of the allyl ether (5 g) N,N-dimethylaniline (70 ml) is stirred under reflux for 5½ hours and cooled slowly to 25° C. The reaction mixture is diluted with hexane and chilled in an ice bath. The resulting precipitate is filtered, washed with hexane and dried affording the desired products as crystalline needles. M.P. 189°-190° C.

Step 7. Methyl 3-allyl-2-methoxy-4-acetylamino-5-chlorobenzoate

A mixture of the phenolic compound of step 6 above (4 g) and NaH (0.7 g) in DMF (50 ml) is stirred for 15 minutes. Dimethyl sulfate (2 g) is added and the mixture is stirred for 16 hours. The mixture is partitioned between $CH_2Cl_2$ and $H_2O$, and the organic layer is separated and washed with $H_2O$, dried (MgSO4) and evaporated. The solid residue is twice recrystallized from MeOH-$H_2O$ and chromatographed on silica gel affording the desired product which is used in the next step.

Step 8. 1-Acetyl-5-carbomethoxy-7-chloro-4-methoxyindole

A 2.5% solution of osmium tetroxide in butanol (0.25 ml) is added to a stirred solution of the methoxy compound from step 7 above (1.5 g) in $H_2O$-dioxane (15 ml/45 ml) and stirred for 30 minutes. Sodium periodate (2.25 g) is added portionwise over one hour and the reaction mixture stirred for 3½ hours. Cyclohexene (1 ml) is added, the mixture stirred for one hour, diluted with $H_2O$ and extracted with CHCl3. The organic layer is separated, dried (MgSO4) and evaporated affording a gum which is dissolved in TFA and allowed to stand for 15 minutes. The acid solution is diluted to 100 mls with $CH_2Cl_2$ and washed with $H_2O$, saturated NaHCO3, dried (MgSO4) and evaporated affording a solid which is chromatographed on silica gel affording a colorless solid which is the indole as confirmed by NMR (270 MHz, CDCl2).

Step 9.
1-Acetyl-5-carbomethoxy-7-chloro-4-methoxy-1,2-dihydroindole

The mixture of the indole of step 8 above (0.9 g) and Pt-C (0.2 g), acetic acid and MeOH (100 ml) is stirred under $H_2$ at 1 atm. pressure for 48 hours. The catalyst is filtered (celite), the filtered material is washed (MeOH) and the reaction mixture and methanol washings are evaporated. The residue is diluted with $CH_2Cl_2$, washed with saturated $NaHCO_3$, dried ($MgSO_4$) and evaporated affording a colorless, semicrystalline material which is determined to be the desired compound by NMR. M.P. 107°–109° C.

Step 10.
1-Acetyl-5-carboxy-7-chloro-4-methoxy-1,2-dihydroindole

A mixture of the indole ester of step 9 above (0.8 g) and 10% aqueous NaOH/MeOH (20 ml/80 ml) is stirred under reflux for 2 hours. The reaction mixture is concentrated and the aqueous residue is diluted with water and extracted with $CHCl_3$. The organic layer is dried ($MgSO_4$) and evaporated affording an off-white solid which is determined to be the desired compound by NMR.

Step 11.
(N-1-azabicyclo[2.2.2]oct-3-yl)-7-chloro-4-methoxy-2,3-dihydroindole-5-carboxamide Ethyl chloroformate (25 ml) is added to a stirred mixture of the acid compound of step 10 above (0.7 g) in $CHCl_3$-$Et_3N$ (25 ml/0.7 g) chilled to $-20°$ C. and stirring is continued for one hour. Aminoquinuclidine (2.8 g) and a saturated aqueous $K_2CO_3$ solution (7 ml) are added to the reaction mixture. Stirring is continued for 2 hours while slowly warning to RT. The mixture is diluted with $CHCl_3$ and $H_2O$, stirred for 5 minutes and the aqueous layer was separated. The organic layer is washed with $H_2O$, dried ($MgSO_4$) and evaporated affording a foamy solid which is converted to the dihydrochloride salt by dissolving in HCl-MeOH and evaporating the solvent. The desired product in the form of the dihydrochloride salt is a hygroscopic material is determined to be the correct material by NMR. M.P.=151°–153° C. Elemental Analysis: Calc'd C: 49.95, H 5.92, N 10.28; Found C: 50.58, H 6.20, N 9.98.

EXAMPLE 2

The Preparation of (N-1-Azabicyclo[2.2.2]oct-3-yl)-8-Chloro-5-Methoxy-1,2,3,4-Tetrahydroquinoline-6-Carboxamide Step 1. Methyl 2-allyloxy-4-amino-5-chlorobenzoate A mixture of methyl 4-amino-5-chlorosalicylate (5 g), allyl bromide (12.6 g), ground $K_2CO_3$ (30 g) and acetone (120 ml) is stirred at reflux for 5 hours and cooled to 25° C. The mixture is partitioned between methylene chloride and $H_2O$, the organic layer is separated, dried ($MgSO_4$), filtered and evaporated. The residue is recrystallized from hexanechloroform affording the desired product as a crystalline solid (M.P. 107°–109° C.).

Step 2. Methyl 3-allyl-2-hydroxy-4-amino-5-chlorobenzoate

A solution of the methyl 2-allyloxy-4-amino-5-chlorobenzoate (3.5 g) N,N-diethylaniline (50 ml) is stirred under reflux for 1.5 hours, cooled, diluted with methylene chloride and washed with 10% aqueous HCl, dried and evaporated affording the desired product as an oil.

Step 3. Methyl 3-allyl-2-methoxy-4-amino-5-chlorobenzoate

A mixture of potassium carbonate (19 g), methyl iodide (8 g) and the phenolic compound of step 2 above (3.4 g) in acetone (100 ml) is stirred under reflux for about 6.4 hours. The mixture is partitioned between $CH_2Cl_2$ and $H_2O$, and the organic layer is separated and washed with 10% aqueous HCl, dried ($MgSO_4$) and evaporated affording an oil which chromatographed on silica gel affording the desired product which is used in the next step.

Step 4. Methyl 3-(3-hydroxypropyl)-2-methoxy-4-amino-5-chlorobenzoate

A mixture of a 1M solution of $BH_3$ in THF(8 ml) and the compound of step 3 above (2 g) in THF-diglyme (10 ml/16 ml) is stirred under $N_2$ for 30 minutes at 20° C. $Me_3NO.2H_2O$ (2.2 g) is added to the mixture and refluxed in a preheated oil bath allowing the THF to evaporate, followed by refluxing the mixture for one hour. The mixture is cooled to 20° C., partitioned between $CHCl_3$ and sat'd aqueous $NaHCO_3$, and stirred for 30 minutes. The organic layer is separated, washed with $H_2O$, dried ($MgSO_4$), evaporated and the residue is chromatographed on silica gel affording the desired product as a solid which is determined to be the correct product by NMR.

Step 5. 6-Carbomethoxy-8-chloro-5-methoxy-1,2,3,4-tetrahydroquinoline

A mixture of the compound of step 4 above (1.4 g), triethylamine (1 ml) and TsCl (1.1 g) in $CH_2Cl_2$ is stirred at 25° C. for three days. The mixture is washed with saturated aqueous $NaHCO_3$ and evaporated affording a residue which is dissolved in toluene and refluxed for 2½ hours. The toluene is evaporated and the residue is dissolved in $CH_2Cl_2$ and washed with saturated $NaHCO_3$ (25 mls). The organic layer is dried, evaporated and the residue chromatographed on silica gel affording a gum which crystallizes from $HexEt_2O$ to give the desired product (M.P. 105°–108° C.).

Step 6. 6-Carboxy-8-chloro-5-methoxy-1,2,3,4-tetrahydroquinoline

A mixture of the compound of step 5 above (1.1 g), 10% aqueous NaOH (20 ml) and MeOH (40 ml) is stirred under reflux for 30 minutes. The MeOH is evaporated and the aqueous residue partitioned with $CHCl_3$. The mixture is stirred vigorously, cooled to 0° C. and treated with 10% HCl (28 mls). The aqueous layer is separated and the organic layer is dried and evaporated. The residue is crystallized from ether affording the desired product, M.P. 129°–132° C.

Step 7. (N-1-azabicyclo[2.2.2]oct-3-yl)-8-chloro-5-ethoxy-1,2,3,4-tetrahydroquinoline-6-carboxamide Ethyl chloroformate (25 ml) is added to a stirred mixture of the acid compound of step 6 above (0.7 g) in $CHCl_3$-$Et_3N$ (25 ml/0.8 g) chilled to $-20°$ C. and stirring is continued for 20 min. Aminoquinuclidine (3.1 g)

and a saturated aqueous K2CO3 solution (6 ml) are added to the reaction mixture. Stirring is continued for 30 minutes while slowly warning to RT. The mixture is diluted with CHCl3 and H2O, stirred for 5 minutes and the aqueous layer was separated. The organic layer is washed with H2O, dried (MgSO4) and evaporated affording a foamy solid which is chromatographed on silica and converted to the hygroscopic hydrochloride salt of the desired product, M.P. 160° C. Elemental Analysis: Calc'd C 55.96, H 6.52, N 10.88; Calc'd(as Hydrate) C 53.47, H 6.73, N 10.39; Found C 53.45, H 7.34, N 10.26. The dihydrochloride salt has the same melting point and the following elemental analysis: Calc'd C 51.13, H 6.20, N 9.94; Found C 51.41, H 6.92, N 10.15.

EXAMPLE 3

The Preparation of
(N-1-Azabicyclo[2.2.2]oct-3yl)-9-Chloro-6-Methoxy-2,3,4,5-Tetrahydrobenzo(1H)-1-Azepine-7-Carboxamide Step 1. 2-(1-Oxo-3-carboxypropyl)-4-chloroanisole A mixture of 4-chloroanisole (20 g), succinic anhydride (16 g) and AlCl3 (42 g) in 1:1 tetrachloroethylene/nitrobenzene (200 ml) is stirred at −10°–0° C. for a week. The mixture is poured into a conc. HCl/crushed ice bath and the solvent is distilled under vacuo at 40° C. The resulting suspension is made basic with 10% aqueous NaHCO3. The solids are filtered and the filtrate made acidic forming a precipitate which is filtered, washed with water, taken up in ethanol and dried. The solution is filtered and evaporated affording the desired product as a white solid, M.P. 113°–115° C.

Step 2. 2-(3-Carboxypropyl)-4-chloroanisole

The acid compound of step 1 above is added to a stirring mixture of toluene (22 ml), conc HCl (41 ml), water (17 ml) and the recovered product of mossy zinc (22.2 g) and mercuric chloride (2.2 g) stirred in an aqueous HCl solution for about 10 minutes. The mixture is stirred under reflux for about 16 hours, diluted with water, extracted with ethyl acetate and the organic layer is dried filtered and evaporated. The residue is taken up in 10% aqueous NaOH, and dimethyl sulfate (about 25 ml) added to the mixture which is heated to 80° C. The mixture is stirred at a constant temperature for about 4 hours, cooled, acidified and the resulting precipitate is filtered dried and used in the next step.

Step 3.
8-Chloro-5-methoxy-1,2,3,4-tetrahydronaphthal-1-one

The acid compound of step 2 above (6 g) is added to a solution of phosphorous pentoxide (6.5 g) in methane sulphonic acid (50 g) and stirred at 60°–70° C. for about 2 hours. The reaction mixture is poured into water, extracted with ethyl acetate and the organic extract is washed with 10% aqueous NaHCO3, dried filtered and evaporated affording the desired bicyclic product as an oil.

Step 4.
8-Chloro-5-methoxy-1,2,3,4-tetrahydronaphthal-1-oxime

A mixture of the keto compound of step 3 above (2.6 g), hydroxylamine hydrochloride (0.9 g), pyridine (6 ml) and ethanol (60 ml) is stirred under reflux for about 3 hours. The mixture is poured into 5% aqueous HCl and extracted with ethyl acetate. The organic extract is washed with acid, sat'd NaCl, dried filtered and evaporated affording the desired crude product as an oil which is used in the next step.

Step 5.
9-Chloro-6-methoxy-2,3,4,5-tetrahydro-benzo(1H)-1-azepin-2-one

The oxime compound of step 4 above (6.7 g), phosphorous pentoxide (16 g) and methane sulfonic acid (160 g) are stirred at 90°–100° C. for about an hour. The mixture is poured into ice water, and the resulting precipitate is filtered, the filtered solid washed with water and taken up in methylene chloride. The organic solution is washed with 10% NaHCO3, dried, filtered, evaporated and chromatographed (silica gel) affording the desired product as a solid which is used in the next step.

Step 6.
7-Bromo-9-chloro-6-methoxy-2,3,4,5-tetrahydro-benzo(1H)-1-azepin-2-one

N-Bromosuccinimide (0.1 g) in DMF (5 ml) is added dropwise to a solution of the benzazepine compound of step 5 above (0.15 g) in DMF (1 ml) at 0° C. and the mixture is allowed to equilibrate to RT. The mixture is poured into water, extracted with ether, the extract is washed with 5% aqueous NaOH, water, dried, filtered and evaporated affording the desired product as an oil.

Step 7.
7-Bromo-9-chloro-6-methoxy-2,3,4,5-tetrahydro-benzo(1H)-1-azepine

Borane-THF (0.8 ml of 1M solution) is added dropwise to a solution of the bromobenzazepine compound of step 6 above (0.17 g) in dry THF (0.3 ml) at 0° C. under argon. The mixture is stirred at reflux for about an hour, cooled and conc. HCl (0.3 ml) added. The mixture is diluted with water, a 10% NaOH solution is added and the mixture is extracted with ether. The organic extract is washed with sat's NaCl solution, dried, filtered and evaporated affording the reduced compound as an oil.

Step 8.
7-Carboxy-9-chloro-6-methoxy-2,3,4,5-tetrahydro-benzo(1H)-1-azepine

A solution of the compound of step 7 above (0.08 g) in hexane is added dropwise to a stirring mixture of n-butyl lithium (0.24 ml of 2.5M in hexane) and tetramethylethyldiamine (0.07 ml) at a temperature of 0° C. Carbon dioxide gas is bubbled through the reaction mixture for one hour at 0° C. and stirred at RT overnight. The mixture is diluted with water, conc. HCl added and extracted with ethyl acetate. The ethyl acetate solution is extracted with 10% NaOH, the basic solution made acidic and back extracted with ethyl acetate. The back extracted ethyl acetate solutin is washed with brine, dried and evaporated affording the desired product as an oil.

Step 9.
(N-1-azabicyclo[2.2.2]oct-3-yl)-9-chloro-6-methoxy-2,3,4,5-tetrahydrobenzo(1H)-1-azepine-7-carboxamide Ethyl chloroformate (2.5 ml) is added to a stirred mixture of the acid compound of step 8 above (0.07 g) in CHCl3-Et3N (2.5 ml/0.1 g) chilled to −20° C. and stirring is continued for 20 min. Aminoquinuclidine (0.3 g) and a saturated aqueoud K2CO3 solution (1 ml) are added to the reaction mixture. Stirring is continued for 30 minutes while slowly warning to RT. The mixture is diluted with $CHCl_3$ and $H_2O$, stirred for 5 minutes and the aqueous layer was separated. The organic layer is washed with $H_2O$, dried ($MgSO_4$) and evaporated affording a solid which is chromatographed on silica and converted to the hydrochloride salt of the desired product.

The following compounds are prepared by procedures analogous to those described above.

(N-1-Azabicyclo[2.2.2]oct-3-yl)-7-chloro-2,3-dihydro-2,2-dimethyl-4-methoxyindole-5-carboxamide dihydrochloride, M.P.=150° C., Elemental Analysis: Calc'd C 52.24, H 6.46, N 9.62; Calc'd (as Hydrate) C 50.17, H 6.65, N 9.24; Found C 50.66, H 6.59, N 9.35.

[N-(N',N'-diethylaminoethyl)]-7-Chloro-4-methoxy-2,2-dimethylindole-5-carboxamide, M.P.=148°–150° C. Elemental Analysis: Calc'd C 61.09, H 7.97, N 11.88; Found C 60.78, H 7.73, N 11.63.

N-(1-Azabicyclo[3.3.1]oct-4-yl)-7-chloro-4-methoxy-2,3-dihydroindole-5-carboxamide.

N-(1-Azabicyclo[3.3.1]oct-4-yl)-8-chloro-5-methoxy-1,2,3,4-tetrahydroquindine-6-carboxamide.

N-[2-(diethylamine)ethyl]-8-chloro-5-methoxy-1,2,3,4-tetrahydroquinoline-6-carboxamide.

N-(1-Azabicyclo[2.2.2.]oct-3-yl)-9-chloro-6-methoxy-2,3,4,5-tetrahydrobenzo(1H)-1-azepine-7-carboxamide.

N-(1-Azabicyclo[3.3.1]oct-4-yl)-9-chloro-6-methoxy-2,3,4,5-tetrahydrobenzo(1H)-1-azepine-7-carboxamide.

N-[2-(diethylamino)ethyl]-9-chloro-6-methoxy-2,3,4,5-tetrahydrobenzo(1H)-1-azepine-7-carboxamide.

We have found that the compounds of this invention have gastric prokinetic, anti-emetic activity and lack $D_2$ receptor binding activity and as such possess therapeutic value in the treatment of upper bowel motility and gastroesophageal reflux disorders. Further, the compounds of this invention may be useful in the treatment of disorders related to impared gastrointestinal motility such as retarded gastric emptying, dyspepsia, flatulence, oesophageal reflux, peptic ulcer and emesis. The compounds of this invention exhibit 5-$HT_3$ antagonism and are considered to be useful in the treatment of psychotic disorders such as schizophrenia and anxiety and in the prophylaxis treatment of migraine and cluster headaches. We have further found that these compounds are selective in that they have little or no dopaminergic antagonist activity.

Various tests in animals can be carried out to show the ability of the compounds of this invention to exhibit pharmacological responses that can be correlated with activity in humans. These tests involve such factors as the emesis, selective antagonism of 5-$HT_3$ receptors and their $D_2$ dopamine receptor binding properties.

It has been found that the compounds of this invention when tested in the above variety of situations show a marked activity.

One such test is the "Rat Gastric Emptying: Amberlite Bead Method". This test is carried out as foillows:

The study is designed to assess the effects of a test agent on gastric emptying of a solid meal in the rat. The procedure is a modification of those used in L. E. Borella and W. Lippmann (1980) Digestion 20: 26–49.

Procedure

Amberlite beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N of 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite beads intragastrically. The beads are delivered via a 3 inch piece o PE 205 tubing attached to a 16 gauge tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads $\pm$S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance may be determined using a t-test for independent samples with a probability of 0.05 or less considered to be significant.

In order to demonstrate the ability of the compounds of this invention as anti-emetic agents the following test for "Cisplatin-Induced Emesis in the Ferret" may be used. This test is a modified version of a paper reported by A. P. Florezyk, J. E. Schurig and W. T. Brodner in Cancer Treatment Reports: Vol. 66, No. 1, January 1982.

Cisplatin had been shown to cause emesis in the dog and cat. Florczyk, et al. have used the ferret to demonstrate the same effects.

Procedure

Male castrated, Fitch ferrets, weighing between 1.0 and 1.5 kg have an Indwelling catheter placed in the jugular vein. After a 2–3 day recovery period, the experimental procedure is begun.

30 minutes prior to administration of Cisplatin, ferrets are dosed with the compound in 0.9% saline (i.v.) at a dose volume of 2.0 ml/kg.

45 minutes after administration of Cisplatin, ferrets are again dosed with 0.9% saline (i.v.) mixture at a dose volume of 2.0 ml/kg.

Cisplatin is administered (i.v.) 30 minutes after the first dosing with the 0.9% saline. Cisplatin, 10 mg/kg is administered in a dose volume of 2.0 ml/kg.

The time of Cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to and fro movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 Dopamine Receptor Binding Assay

The D-2 dopamine receptor binding assay has been developed with slight modifications using the method of Ian Cresse, Robert Schneider and Solomon H. Snyder, Europ. J. Pharmacol. 46: 377–381(1977). Spiroperidol is a butyrophenone neuroleptic whose affinity for dopamine receptors in brain tissue is greater than that of any other known drug. It is a highly specific D-1 dopamine (non-cyclase linked) receptor agent with $K_1$ values of 0.1–0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleum (corpus striatum) is used as the receptor source because it contained the highest density of dopamine receptors in the brain and periphery.

Procedure

Male Charles-River rats weighing 250–300 g are decapitated and their brains removed, cooled on ice, and caudate dissected immediately and frozen on dry ice. Tissue can be stored indefinitely at $-70°$ C. For assay caudate is homogenized in 30 ml of tris buffer (pH 7.7 at 25° C.) using the polytron homogenizer. The homogenate is centrifuged at 40,000 g (18,000–19,000 RPM in SS-34 rotor) for 15 minutes. Pellet is resuspended in fresh buffer and centrifuged again. The final pellet is resuspended in 150 volumes of assay buffer.

Specific $^3$H-spiroperidol binding is assayed in a total 2 ml reaction volume consisting of 500 $\mu$l of caudate homogenate, 50 mM tris buffer (pH 7.4 at 35° C.), 5 mM MgSO$_4$, 2 mM EDTA 2NA, 120 mM NaCl, 0.1% ascorbic acid, 0.4 nM $^3$H-spiroperidol and test compound or assay buffer. When catecholamines are included in the assay, 10 $\mu$M pargyline should be included in the reaction mixture to inhibit monoamine oxidase. Samples are incubated at 35° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 $\mu$M D(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248(1976) using Bio-Rad's coomassie blue G-250 dye reagent. Bovine gamma Globulin supplied by BIO-RAD is used as the protein standard.

Bezold-Jarisch effect in anesthetized rats

Male rats 260–290 g are anesthetized with urethane 1.25 g/kg$^{-1}$ i.p., and the trachea cannulated. The jugular vein is cannulated for intravenous (i.v.) injection of drugs. Blood pressure is recorded from a cannula in the left carotid artery and connected to a haparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. injections of 5-HT are given every 12 minutes and a dose-response curve for the test compound is established by injecting increasing doses of compound 5 minutes before each injection of 5-HT. The effect of the compound on the 5-HT-evoked bradycardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 strains with a maximally-effective voltage (20 V at 10 Hz). Pulse frequency may vary from 5–30 Hz and frequency-response curves are constructed before and 10 minutes after i.v. injection of a single dose of compound.

The results of these above tests indicate that the compounds for this invention exhibit a valuable balance between the peripheral and central action of the nervous system and may be useful in the treatment of disorders related to impaired gastro-intestinal motility such as gastric emptying, dyspepsia, flatulence, esophageal reflux and peptic ulcer and in the treatment of disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelating; excipients such as dicalcium phosphate; a disintegrating agent such as corn starch, potato starch, alginic acid and the like; a lubricant such as magnesium stearate; and a sweetening agent such as sucrose, lactose of saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperiotoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agent delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compound of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 5 mg/kg of body weight per day and higher although it may be administered in several different dosage units from once to several times a day. Higher dosages are required for oral administration.

We claim:

1. A compound of the formula

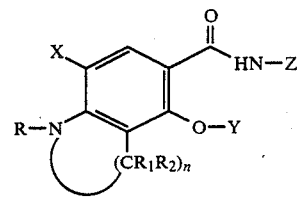

wherein:
X is hydrogen, hydroxy, amino, mono- and di-loweralkylamino, halo, trifluoromethyl, sulfamyl, mono- and di-loweralkylsulfamyl or loweralkylsulfonyl;
R is hydrogen or loweralkyl;
$R_1$ and $R_2$ are independently hydrogen or loweralkyl;
vicinal $R_2$ groups together may be, $-(CH_2)_a-$ where a is 1 to 4, thus forming a 3 to 6 membered ring;
n is 2 to 4;
Y is loweralkyl, $-(CR_1R_2)_b$-SO-loweralkyl or $-(CR_1R_2)_b$-CO-loweralkyl;
b and d are 1 to 3; and
Z is $-(CR_1R_2)_d-NR_1R_2$,

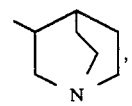

N, or

-continued

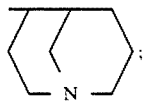

or a pharmaceutically acceptable salt thereof.

2. A compound according to claim 1 wherein:

X is hydrogen or halo;

R is hydrogen, methyl or ethyl;

$R_1$ and $R_2$ are independently hydrogen, methyl or ethyl;

Y is methyl, ethyl, propyl, i-propyl, butyl, i-butyl, sec-butyl, t-butyl, pentyl, —$(CR_1R_2)_b$-SO-loweralkyl of 1-3 carbon atoms, —$(CR_1R_2)_b$-CO-loweralkyl of 1-3 carbon atoms;

b is 1 to 3; and

Z is

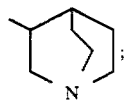

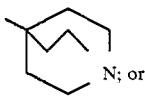

-continued

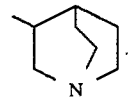

or a pharmaceutically acceptable salt thereof.

3. A compound according to claim 1 wherein

X is chloro or bromo;

R is hydrogen or methyl;

$R_1$ and $R_2$ are independently hydrogen, methyl or ethyl;

Y is methyl; and Z is

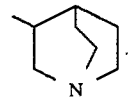

4. A compound according to claim 1 which is (N-1-azabicyclo[2.2.2]oct-3-yl)-7-chloro-4-methoxy-2,3-dihydroindole-5-carboxamide or a pharmaceutically acceptable salt thereof.

5. A compound according to claim 1 which is (N-1-azabicyclo[2.2.2]oct-3-yl)-8-chloro-5-methoxy-1,2,3,4-tetrahydroquinoline-6-carboxamide or a pharmaceutically acceptable salt thereof.

6. A compound according to claim 1 which is (N-1-azabicyclo[2.2.2]oct-3-yl)-9-chloro-6-methoxy-2,3,4,5-tetrahydro-benzo(1H)-1-azepine-7-carboxamide or a pharmaceutically acceptable salt thereof.

7. A compound according to claim 1 which is (1-azabicyclo[3.3.1]non-4-yl)-8-chloro-5-methoxy-1,2,3,4-tetrahydroquinoline-6-carboxamide or a pharmaceutically acceptable salt thereof.

* * * * *